United States Patent [19]

Nolan et al.

[11] Patent Number: 5,728,572
[45] Date of Patent: Mar. 17, 1998

[54] GROWTH MEDIA FOR ENTOMOPHTHORALEAN HYPHAL BODIES

[76] Inventors: Richard A. Nolan, deceased, late of St. John's, Canada; by Anna Nolan, executrix, 13 Wishingwell Road, St. John's, Newfoundland A1B 1G4, Canada

[21] Appl. No.: 329,470

[22] Filed: Oct. 26, 1994

Related U.S. Application Data

[63] Continuation-in-part of Ser. No. 8,350, Jan. 22, 1993, abandoned.
[51] Int. Cl.⁶ .................................. C12N 1/14; C12N 1/16
[52] U.S. Cl. .............................. 435/254.1; 435/256.8
[58] Field of Search ......................... 424/93.5; 435/254.1, 435/256.8

[56] References Cited

U.S. PATENT DOCUMENTS 4,751,082   6/1988   Schaeffenberg et al. ............. 424/93.5

OTHER PUBLICATIONS

Dunphy et al. Can J. of Microbiology, 35(2) 1989, pp. 304–308.

Murrin et al. Can J of Botany, 65(8), 1987 1694–1706.

*Primary Examiner*—Irene Marx
*Assistant Examiner*—L. Blaine Lankford
*Attorney, Agent, or Firm*—Marcus & Associates

[57]   ABSTRACT

A process is provided for the fermentation production of hyphal bodies which form conidia of species of the fungal order Entomophthorales, especially *Entomophaga aulicae*. The process uses an improved growth medium. The improved mediuem includes, in addition to a basal medium, filter-sterilized tryptic soy broth and calcium caseinate. Such medium allows the use of a protoplast and/or a walled stage inoculum in a batch fermentation process.

4 Claims, 4 Drawing Sheets

GROWTH MEDIA FOR ENTOMOPHTHORALEAN HYPHAL BODIES

RELATED APPLICATION

This application is a continuation-in-part of application Ser. No. 08/008,350 filed Jan. 22, 1993, now abandoned, the entire contents of which are incorporated herein by reference.

BACKGROUND OF THE INVENTION (a) Field of the Invention

This invention relates to an improved medium for mass fermentation production of entomophthoralean (Zygomycetes, Entomophthorales), and especially *Entomophaga aulicae* hyphal bodies which form conidia by supporting the development of the fungus from a protoplast through to walled hyphal body and conidial stages.

(b) Description of the Prior Art

Defoliation by insect larvae causes major economic losses in the forestry industry of North America. *Entomophaga aulicae* is a naturally-occurring pathogen of the larvae of three major forest defoliators and is being developed as a biocontrol agent for the eastern hemlock looper and the eastern spruce budworm. Chemical insecticides and the bacterium *Bacillus thuringiensis* are currently used against the larvae of these defoliators. The chemicals are highly toxic and potentially harmful to forest ecosystems. *Bacillus thuringiensis* gives erratic results and is not a normal component of these forest ecosystems. *E. aulicae* is a normal component of the forest ecosystems and has caused the collapse of target insect infestations. Protoplasts are the initial and only developmental stages within the larval haemocoel until the walled hyphal bodies are formed (see, Murrin and Nolan, Can. J. Bot. 65:1694–1706, 1987). The hyphal bodies produce emergent conidiophores which, in turn, produce the infective conidia external to the cadaver. Thus, mass production and dissemination of hyphal bodies would seem to be an effective means of supplementing low levels of the fungus in the field during outbreaks when larval stages of eastern hemlock looper and/or eastern spruce budworm are present.

Entomophthoralean species are known to cause large scale epizootics and to produce resting spores which might be stored for long periods. Consequently, these fungi are excellent candidates for use in biological control. However, the practical utilization of entomophthoralean species as biological control agents has been hampered by the inability to produce hyphal bodies which form conidia. In many representatives of the Entomophthorales, hyphal bodies are initially produced by hyphal fragmentation but may subsequently undergo fission or budding.

Many papers have been published which relate to fermentation media or other media for the growth of *Entomophaga aulicae*.

For example, one paper taught the productions of high yields of *Entomophthora thaxteriana* resting spores at the 20 L fermentation level using a 4% glucose+1% peptone+0.5% yeast extract medium. A 3% corn syrup+0.5% peptone (peptic digest of meat) medium also produced resting spores. [see Groner (J. Invertebr. Pathol. 26:393–394, 1975)].

In addition, hyphal bodes of *E. aulicae* have been produced in trehalose-yeast extract and glucose-casamino acids based media in small scale cultures. Resting spores were induced to form septate hyphae at pH 8.5 (see, Nolan et al., Can. J. Bot. 54:1131–1134, 1976).

*E. aulicae* hyphal bodies have also been formed in a medium containing glucose-yeast extract, or in a medium containing glucose-yeast extract-lactalbumin hydrolysate-fetal calf serum (see, Beauvais and Latge, J. Invertebr. Pathol. 51:175–178, 1988).

The potential for manipulating the types and proportion of *E. aulicae* hyphal bodies using a fungal sex hormone and a synthetic insect juvenile hormone has also been described (see, Nolan and Dunphy, J. Invertebr. Pathol. 33:242–248, 1979).

A review paper describing protoplast production for entomophthorales species in various complex medium has been published [see, "Fungal Protoplasts—Application in Biochemistry and Genetics", edited by J. F. Peberdy et al, Marcel Dekker, Inc., 1985, pages 87 to 112, "Protoplasts from Entomophthorales", by R. A. Nolan].

Nolan, in Can. J. Microbiol. 32:855–860, 1986, in an article entitled "Effects of an Altered Developmental Pattern on Amino Acid Uptake For a Protoplast Isolate of the Fungus *Entomophaga aulicae* Under Mass-Fermentation Conditions" described the use of the following fermentation medium:

| Composition of fermentation medium | | | |
|---|---|---|---|
| Compound | Concn. gm/10 L* | Compound | Concn. gm/10 L* |
| NaH$_2$PO$_4$.H$_2$O† | 10.13 | Glucose† | 7.0 |
| KCl | 41.0 | Malic acid† | 6.7 |
| CaCl$_2$.2H$_2$O | 11.1 | Succinic acid† | 0.6 |
| MgCl$_2$.6H$_2$O | 22.8 | α-Ketoglutaric acid† | 3.7 |
| MgSO$_4$.7H$_2$O | 27.8 | Fumaric acid | 0.56 |
| NaHCO$_3$† | 3.5 | MES | 19.5 |
| L-Asparagine.H$_2$O | 4.0 | Fetal calf serum, mL | 280 |
| L-Aspartic acid | 3.5 | Thiamine hydrochloride, mg/10 L | 0.2 |
| L-Glutamine† | 6.0 | Riboflavin, mg/10 L | 0.2 |
| L-Leucine† | 1.52 | Calcium pantothenate, mg/10 L | 0.2 |
| L-Methionine | 0.5 | Pyridoxine hydrochloride, mg/10 L | 0.2 |
| L-Proline | 3.5 | p-Aminobenzoic acid, mg/10 L | 0.2 |
| DL-Serine | 5.5 | Folic acid, mg/10 L | 0.2 |
| L-Threonine | 1.75 | Niacin, mg/10 L | 0.2 |
| L-Tyrosine | 0.5 | i-Inositol, mg/10 L | 0.2 |
| Sucrose† | 275.0 | Biotin, mg/10 L | 0.1 |
| Fructose† | 4.0 | Choline chloride, mg/10 L | 0.2 |

*Except where noted.
†Filter sterilized.

Doern et al, [J. of Clinical Micro. 24(4), 507–511 (October 1986)], taught the effect of medium composition on the susceptibility of yeast to four antifungal agents. Among the six media evaluated were:

1) SAAM-F, i.e., synthetic amino acid medium fungi;

3) BYNB, i.e., buffered yeast nitrogen broth;

3) Kimmney broth;

4) CYG, i.e., casein-yeast-glucose broth;

5) ANTI-3, i.e., antibiotic medium 3-FDA;

6) TSB, i.e., tryptic soy broth alone.

The results of these evaluations by Doern et al showed that, for antifungal susceptibility testing of yeasts to antifungal agents, the use of TSB alone gave the least favorable results. There was no teaching by Doern et al of any correlation between the growth of entomophthorales hyphal bodies and any of the media evaluated in their tests. There was no suggestion in Doern et al to lead any person to add TSB to a conventional, (i.e., Grace's medium), growth medium.

Furthermore, Doern et al taught that the TSB used in their evaluations was prepared according to the recommendation of the manufacturers. The manufacturer of TSB, (i.e., Tryptic Soy Broth, soybean-casein Digest Medium, USP), is Difco Laboratorie, who describe the TSB as a general purpose medium for the cultivation of fastidious and non-fastidious microorganisms. The formula of TSB, as provided by the manufacturer, was:

| FORMULA | |
|---|---|
| Ingredients per liter | |
| Bacto-Tryptone<br>Pancreatic Digest of Casein | 17 g |
| Bacto-Soytone<br>Papain Digest of Soybean Meal | 3 g |
| Bacto-Dextrose | 2.5 g |
| Sodium Chloride | 5 g |
| Dipotassium Phosphate | 2.5 g |

The direction for rehydration of TSB, as provided by the manufacturer, were "to rehydrate, suspend 30 grams in 1 liter distilled or deionized water, warm slightly to dissolve completely, dispense as desired and sterilize in the autoclave for 15 minutes at 15 pounds pressure (121° C.)".

Another medium has been developed for the mass fermentation growth of lepidopteran (*Spodoptera frugiperda*) cells in the absence of sera. Its development was predicated upon the assumptions that albumin is functionally the most important component of sera and that the critical attribute of albumin is its binding of fatty acids; however, the absence of a requirement for an external source of fatty acids has been established for *E. aulicae* (see Nolan, Can. J. Microbiol. 34:45–51, 1988).

Another paper which has been published described the growth of *Entomophaga aulicae* and taught that protoplasts were the initial and only developmental stages within the larval haemocoel until the walled hyphal bodies are formed. [see Murrin and Nolan, Can. J. Bot. 65:1694–1706, 1987].

Nolan, in Can. J. Microbiol. 34:45–51, 1988, in an article "A Simplified, Defined Medium For Growth of Entomophaga aulicae Protoplasts" described the use of the following medium:

| Composition of eight amino acid (8 AA) medium | | | |
|---|---|---|---|
| Compound | Concn.<br>(g/L)ᵃ | Compound | Concn.<br>(g/L)ᵃ |
| $NaH_2PO_4.H_2O$ | 1.01 | L-Leucine | 0.075 |
| KCl | 4.10 | L-Methionine | 0.05 |
| $CaCl_2.2H_2O$ | 0.75 | L-Phenylalanine | 0.15 |
| $MgCl_2.6H_2O$ | 2.28 | L-Threonine | 0.175 |
| $MgSO_4.7H_2O$ | 2.78 | Glucose | 0.70 |
| $NaHCO_3$ | 0.35 | Sucrose | 32.10 |
| L-Aspartic acid | 0.35 | MES | 1.95 |
| L-Glutamic acid | 0.60 | Hematin (µg/mL) | 0.50 |
| Glycine | 0.65 | Oleic acid (µg/mL) | 1.0 |
| L-Histidine | 2.50 | $Na_2EDTA$ (mM) | 0.032 |
| | | Micronutrients (mL/L) | 1.0ᵇ |

ᵃExcept where noted.
ᵇSee Nolan (1970b).

which was a highly simplified and modified version of Grace's medium [Grace, Nature(London), 195:788–789, 1962]:

TABLE 1

| Composition of Grace's medium* | | | |
|---|---|---|---|
| Compound | Concn.<br>(g/L)ᵇ | Compound | Concn.<br>(g/L)ᵇ |
| $NaH_2PO_4.H_2O$ | 1.01 | DL-Serine | 1.10 |
| KCl | 4.10 | L-Threonine | 0.175 |
| $CaCl_2.2H_2O$ | 0.75 | L-Tryptophan | 0.10 |
| $MgCl_2.6H_2O$ | 2.28 | L-Tyrosine | 0.05 |
| $MgSO_4.7H_2O$ | 2.78 | L-Valine | 0.10 |
| $NaHCO_3$ | 0.35 | Glucose | 0.70 |
| β-Alanine | 0.20 | Fructose | 0.40 |
| L-Alanine | 0.225 | Sucrose | 26.68 |
| L-Arginine HCl | 0.70 | α-Ketoglutaric acid | 0.37 |
| L-Asparagine.$H_2O$ | 0.40 | Fumaric acid | 0.056 |
| L-Aspartic acid | 0.35 | Malic acid | 0.67 |
| L-Cystine | 0.022 | Succinic acid | 0.06 |
| L-Glutamic acid | 0.60 | Thiamine HCl, mg/L | 0.02 |
| L-Glutamine | 0.60 | Riboflavin, mg/L | 0.02 |
| Glycine | 0.65 | Ca pantothenate, mg/L | 0.02 |
| L-Histidine | 2.50 | Pyridoxine HCl, mg/L | 0.02 |
| L-Isoleucine | 0.05 | p-Aminobenzoic acid, mg/L | 0.02 |
| L-Leucine | 0.075 | Folic acid, mg/L | 0.02 |
| L-Lysine HCl | 0.625 | Niacin, mg/L | 0.02 |
| L-Methionine | 0.05 | iso-Inositol, mg/L | 0.02 |
| L-Phenylalanine | 0.15 | Biotin, mg/L | 0.01 |
| L-Proline | 0.35 | Choline chloride, mg/L | 0.20 |
| | | MES | 1.95 |

*Adapted from Grace (1962).
ᵇExcept where noted.

Grace's medium as disclosed in Dunphy et al, [Canadian Journal of Micro, 35(2), 304–308 (Feb. 1989)], did not contain either tryptic soy broth or calcium caseinate. The disclosure of this Dunphy et al reference was a report on a study which was done using stationary (i.e., non-shaken) cultures. The major problem with this reported study was that it was a "dead-end" study and could not easily be carried beyond the small-scale [50mL medium/125 stationary flask level (see legends for FIGS. 1A,C)]. This was primarily because of the production of the spherical mesoprotoplasts and the elliptical mesoprotoplasts, both of which possessed numerous cytoplasmic extensions (see FIGS. 1,2; and also Dunphy and Nolan, Can. J. Bot. 55:3046–3053, 1977) which would be torn off by the shear forces in a fermentation vessel. This study would not suggest production of *Entomophaga aulicae* in a fermentation vessel.

In addition, Table 3 in the Dunphy et al paper deals with the levels of 12 amino acids and amines (including ammonia) during 1167 h of incubation, when, in fact, the experiment was run for 245 h (see p. 306, right column, line 14) and 19 amino acids were present in the final medium after the uptake/utilization patterns of 25 such compounds was tested.

Nolan, in Can. J. Bot. 68:2708–2713, 1990, in a paper "Enhanced Hyphal Body Production by *Entomophaga aulicae* Protoplasts in the Presence of a Neutral and a Positively Charged Surface Under Mass Fermentation Conditions" described the use of a modified Grace's medium to which 13 amino acids were added and from which the organic acids and fructose had been deleted, but which had been supplemented with fetal calf serum.

Nolan, in Can. J. Bot. 69:2578–2581, 1991, in a paper "Influence of a Negatively Charged Surface (TEFLON™ Disk) on *Entomophaga aulicae* Protoplast Morphogenesis Under Mass Fermentation Conditions" described the use of a modified Grace's medium supplemented with heat-inactivated fetal calf serum and with sucrose as the osmotic stabilizer.

More recently, a paper has been presented which discussed recent advances in fermentation media development for the fermentation of *Entomophaga aulicae*. [see Nolan, "Mass Fermentation Products of Entomophtoga Aulicae Stages for Forest Insect Control", Abstract of paper presented at 42nd Annual Canadian Society of Microbiologists Meeting, St. John's, Newfoundland, Jun. 14 to 18, 1992].

The patent literature has also provided a teaching of the production of Entomophthora and other species under other than mass fermentation conditions.

U.S. Pat. No. 3,025,221 patented Mar. 13, 1962 by A. Ciegler et al taught the use of a medium having the following ingredients: acid-hydrolyzed soybean meal, acid-hydrolyzed corn meal, choice white grease, non-ionic detergent, thiamin HCl and tap water for the purpose of improving beta-carotene production by mycelia of the fungus *Blakeslea trispora*.

U.S. Pat. No. 3,025,221 patented Mar. 13, 1962 by A. Ciegler et al, taught the use of a medium having the following ingredients: acid-hydrolyzed soybean meal, acid-hydrolyzed corn meal, choice white grease, non-ionic detergent [a tertiary octylphenoxy poly(ethylenoxy) ethanol], thiamin HCl and tap water for the purpose of improving beta-carotene production by mycelia of the fungus *Blakeslea trispora*.

U.S. Pat. No. 3,071,519 patented Jun. 1, 1963 by A. Bonnefoi taught the production of substances adapted biologically to destroy caterpillars and further pests which produce havoc in cultures and forests. The substance was *Bacillus thuringiensis*, which was cultured in a liquid medium containing animated nitrogen and at least one glucide and also containing, as a trace element, at least one metal selected from the group consisting of calcium, zinc, manganese and magnesium.

U.S. Pat. No. 3,151,038 patented Sep. 29, 1964 by W. D. Gray teaches the use of two different media for the production of protein by cells (e.g., mycelia or fungal tissue) of representatives of the class Fungi Imperfecti (Deuteromycetes) and the *Mycelia Sterilia*. One medium comprised a source of assimilable carbohydrate; a nitrogen source, e.g., a water-soluble inorganic nitrogen source, or a non-protein organic nitrogen source; and a zinc salt.

U.S. Pat. No. 3,300,390 patented Jan. 24, 1967 by J. D. Tiner et al taught a method for the production and harvesting of microbial (mold and actinomycete) spores. The culturing of the selected molds was carried out in accordance with conventional methods employing conventional culture media for these organism, e.g., potato dextrose agar, or agar admixed with modified Czapek's broth of difco mycological broth and agar. This growing of the mold or fungus on the solid air-exposed nutrient substrate was continued until sporulation had occurred to the desired extent. The intermingled mycelium and spores were submerged in a liquid medium. Entrapped gases were removed from the submerged material. The liquid medium and contained submerged material was then subjected to the action of ultrasonic vibrations to liberate the spores from the desporulated mycelium. Finally the desporulated mycelium was separated and removed from the spores.

U.S. Pat. No. 3,394,008 patented Jul. 23, 1968 by J. Lodder et al taught the use of a medium having a composition of: a molasses mixture (about 20% cane molasses and about 80% beet molasses), saccharose and a nitrogen source for use in the growth of various strains of the yeast *Saccharomyces cerevisiae*.

U.S. Pat. No. 3,616,245 patented Oct. 26, 1971 by E. O. Stapley et al taught that increased yields of the antibiotic (−) (cis-1,2-eposypropyl)-phosphonic acid were obtained by the addition of certain carboxylic acids to fermentation media.

U.S. Pat. No. 3,766,685 patented Oct. 23, 1973 by W. J. Nickerson et al taught the production of soil conditioners by the fermentation of used tire mesh. The growth medium included trace metals, e.g., phosphorous, magnesium and potassium, tire mesh, and a small amount of ethanol. One suitable medium was the Taber and Vining medium which may be modified by the substitution of 0.01 per cent yeast extract for the vitamin source.

U.S. Pat. No. 3,870,600 patented Mar. 11, 1975 by K. A. Youssef taught a selective enrichment nutrient medium for the isolation, identification and propagation of yeasts and fungi. The medium contained a fruit pulp, or quinone derivative(s), a source of nitrogen, minerals and sugar. Another such nutrient medium contained bactopeptone, sodium nitrate, beef extract, dextrose and agar.

R. S. Soper, Jr., in U.S. Pat. No. 4,021,306 patented May 3, 1977 and U.S. Pat. 4,026,765 patented May 31, 1977 each described the production of Entomophthora resting spores by modifying an egg yolk medium with a particular maltose agar, i.e., Sabouraud maltose agar containing the following ingredients per liter: 10 gm. polypeptone (a pancreatic digest of casein and a peptic digest of animal tissue), 40 gm. maltose and 15 gm. agar. The resting spores were preconditioned at harvest time by contact with ethanol (95%), high speed blending, sonication or by a combination of ethanol contact and high speed blending. This resulted in increased germination of the spores at levels up to 100%.

U.S. Pat. No. 4,212,947 patented Jul. 15, 1980 by A. K. Torev provided a teaching for the production of certain mutants of the basidiomycetes *Polyporus sguamosus* and *Polyporus brumalis* in a medium composed of: 4–5% molasses, 0.2% $NH_4NO_3$ and 0.12% $KH_2PO_4$ plus a foam suppressant (0.04% vegetable oil). The mycelium produced was felt to be useful as a food or a food additive.

French Patent 2,494,717 patented May 28, 1982 by J.-P. Latge and D. F. Perry taught a medium for the production of entomophthoralean resting spores which utilized a mycelial (24–72 hour old) inoculum. This medium consisted of yeast extract and glucose.

U.S. Pat. No. 4,370,159 patented Jan. 25, 1983 by R. B. Holtz taught the use of a medium, in particle form, containing soy protein concentrate, calcium caseinate, sodium acetate, soy and/or cottonseed oil, lecithin and water for use in enhancing the growth of fungal mycelia and, in particular, for increasing the growth and yield of mushrooms. In this invention the nutrient particles resisted breakdown during early mycelial growth in order to be available to the later mycelia near to the time of fruiting body formation. The calcium caseinate and sodium acetate promoted mushroom growth by acting as nutrients and by stimulating enzyme production and/or activity or other growth processes. The soy protein concentrate, used in a denatured form, functioned to form the matrix of the particles cles which were difficult for the mycelia to break down and which encapsulated the nutrients.

U.S. Pat. No. 4,421,543 patented Dec. 20, 1983 by R. B. Holtz taught the use of a medium, in particle form, containing soy protein concentrate, calcium caseinate, sodium acetate, soy and/or cottonseed oil, lecithin and water for use in enhancing the growth of fungal mycelia and, in particular, for increasing the growth and yield of mushrooms. The nutrient particles were said to have resisted breakdown during early mycelial growth in order to be available to the later mycelia near to the time of fruiting body formation. The calcium caseinate and sodium acetate were said to have promoted mushroom growth by acting as nutrients and by stimulating enzyme production and/or activity or other growth processes. The soy protein concentrate, used in a denatured form, was said to have functioned to form the matrix of the particles which were difficult for the mycelia to break down and which encapsulated the nutrients.

Accordingly, this patent taught the use of a matrix consisting of denatured protein which holds enhancer droplets for use by mushroom mycelia (column 1, 1.32) late in their growth in compost beds (col. 1, 1.43-43; col. 6, 1.60-63). This patent dealt with a fungus with walls in a non-shear environment. The emphasis was on denaturing the soy meal protein (col. 3, 1.52-58) in the matrix by dehydration followed by exposure to formaldehyde and heat (col. 4, 1.12-19) in order to render the matrix difficult for young mycelia to break down (col. 2, 1.63-65) to access the enhancer droplets. The enhancer droplets consisted of five types of starting materials, typically: soy protein concentrate, soy/ and or cottonseed oil, lecithin, calcium caseinate, sodium acetate and water (col. 5, 1.39-48; col. 5, Table 1). The enhancer droplets consist of an outer layer of non-denatured soy protein which can be utilized as a nutrient (col. 4, 1.58-62). Inside this protein layer were found the activator materials which consisted of calcium caseinate and sodium acetate (col. 4, 1.65-67). The activator materials were said to have activated or catalized enzyme construction and/or other cell growth processes (col. 5, 1.1-5). In addition, lecithin, sodium acetate, and calcium caseinate were said to have acted together to stimulate mycelial growth and enzymes (col. 7, 1.29-35). Thus, the roles of calcium caseinate, sodium acetate, and lecithin were taught to be overlapping and inseparable. Their overall function was said to be the greater utilization of the nutrients in the compost and in increasing mushroom production (col. 7, p.38-40).

Consequently, there was no teaching of the effect of calcium caseinate alone on a fermentation medium. The patentee taught the utility of enhancer droplets containing a combination of five active ingredients, namely soy protein concentrate, calcium caseinate, sodium acetate, soy and/or cottonseed oil and lecithin. Thus, this patentee only taught the effect of calcium caseinate plus four other ingredients. This patent would have taught that it would be desirable to add soy protein concentrate, calcium caseinate, sodium acetate, soy and/or cottonseed oil and lecithin, as well as calcium caseinate to a growth medium. There is no teaching in Holtz of what the effect of the addition of calcium caseinate alone to Grace's medium might be.

U.S. Pat. No. 4,530,834 patented Jul. 23, 1985 by D. McCabe and R. S. Soper, provided still other teachings with respect to entomophthoralean fungi. The patented process for harvesting mycelia to retain viability included the following steps: the liquid medium was discarded and the mycelia resuspended and slurried in a volume of water. The slurry was then filtered on a vacuum apparatus to obtain a thin, moist, mycelial sheet. The mats were then treated with a chemical protectant to prevent excessive loss of viability during storage, placed on racks at room temperature (about 22° C., 20–40% relative humidity) and allowed to stand for 4–5 hrs. The mats were then incubated at 4° C., 95–98% relative humidity for 12–18 hrs. Following this cold incubation, the mats were dried at room temperature under forced draft, then powdered and stored. For insect control, the product of this process was formulated as a wettable powder and sprayed on plants. The fungus was harvested while in the active growth phase.

U.S. Pat. No. 4,818,268 patented Apr. 4, 1989 by R. B. Holtz, taught the use of a water soluble phosphoglyceride, e.g., hydroxy lecithin and betaine or choline as an osmoprotectant for use in conjunction with the inventions of U.S. Pat. Nos. 4,370,159 and 4,421,543 by the same patentee.

French Patent 2,639,230 patented May 25, 1990 by A. Beauvais and J.-P. Latge taught the production of an inhibitor of $\beta(1\text{-}3)$ glucan synthase activity by protoplasts of representatives of the Entomophthorales. For growing representatives of the Entomophthorales studied, except *Entomophaga aulicae*, a medium composed of glucose, lactalbumin hydrolysate, yeast extract and NaCl was used. In the case of *E. aulicae*, the patentees claimed that this fungus required the addition of a minimum concentration of 5% fetal calf serum to the medium for protoplast growth.

U.S. Pat. No. 5,077,201 patented Dec. 31, 1991 by J. Eyal and M. G. Spencer, taught the use of a medium containing the following ingredients: glucose (or other carbon sources), $MgSO_4.7H_2O$, [casamino acid, yeast extract, soytone (or other nitrogen sources)], $NH_4NO_3$, $KH_2PO_4$, $CaCl_2.2H_2O$, $CuSO_4$, $FeCl_3.6H_2O$, $MnSO_4.4H_2O$, $Na2MoO_4.2H_2O$, $ZnSO_4.6H_{20}$ and thiamine HCl for the production of a pigment by a strain of *Morchella rotunda*.

U.S. Pat. No. 5,077,201 patented Dec. 31, 1991 by J. Eyal et al taught the use of a medium containing the following ingredients: glucose (or other carbon sources), $MgSO_4.7H_2O$, [casamino acid, yeast extract, soytone (or other nitrogen sources)], $NH_4NO_3$, $KH_2PO_4$, $CaCl_2.2H_2O$, $CuSO_4$, $FeCl_3.6H_2O$, $MnSO_4.4H_2O$, $Na_2MoO_4.2H_2O$, $ZnSO_4.6H_2O$ and thiamine HCl for the production of a pigment by a strain of *Morchella rotunda*.

U.S. Pat. No. 5,100,789 patented Mar. 31, 1992 by H. Yamashita et al taught the addition of peptone originating from casein plus corn steep liquor to a medium containing additional organic nitrogen sources, surfactants, phosphates, inorganic salts containing: potassium, magnesium and calcium and a carbon source (e.g. glucose or sucrose) for the production of mevalonic acid by *Saccharomycopsis fibuligera*.

Consequently, as pointed out above, the patent literature also taught a wide variety of media for use with other microorganisms under a wide range of growth conditions and, as in the case with fungi, those who are skilled in the art will recognize that not all of the media components will be represented because of a demonstrated requirement(s) by all of the organism(s).

SUMMARY OF THE INVENTION (a) Aims of the Invention

Heretofore, therefore it was thought that, since the resting spore was responsible for long term survival of fungi, it was the most desirable stage to produce, formulate and apply for insect control. The major problem has been to develop suitable methods to break resting spore dormancy. The use of other stages of the fungi was believed to be impractical since they could not be produced in any way which would allow storage.

In view of the problems associated with the media used heretofore, and as described above, the main object of the present invention is to provide a mass fermentation medium which can serve as the basis for media for growth and morphogenesis of Entomophthoralean fungi. According to the present invention, *Entomophaga aulicae* has been used in the development of this medium because of its more exacting growth requirements. With the use of this medium the *E. aulicae* developmental sequence from protoplast inoculum to hyphal bodies which form conidia can be carried out in a batch fermentation process. By examining the fermentation product, it can be determined if conidia can be produced prior to engaging in costly field spraying. This medium has been found to support the growth of *E. aulicae* isolates from widely separated ge medium is relatively inexpensive. The hyphal bodies are easily separated from the spent growth medium. The hyphal body yield is high. Finally, the hyphal bodies can withstand a variety of spray techniques.

(b) Statements of Invention

The present invention therefore provides, in its broadest aspect, an improvement in a process for the mass fermentation production of hyphal bodies to form conidia of the fungal order Entomophthorales, e.g., *E. aulicae*, the improvement of including, in addition to a basal medium, an additive consisting essentially of both 0.8% by weight filter sterilized tryptic soy broth and 0.4 by weight calcium caseinate, thereby to provide a total fermentation medium for developing a mixed protoplast inoculum through a series of protoplast stages to form walled spherical and rod-shaped hyphal bodies, which then form conidia from the protoplast inoculum.

(c) Other Features of the Invention

By one feature of the process of this invention, the composition of the basal medium for the fermentation of *E. aulicae* is as follows:

| Compound | Concentration g/10 L |
|---|---|
| $NaH_2PO_4.H_2O$ | 10.13 |
| KCl | 41.0 |
| $CaCl_2$ | 7.5 |
| $MgCl_2.6H_2O$ | 22.8 |
| $MgSO_4$ | 13.5 |
| $NaHCO_3$ | 3.5 |
| L-Asparagine | 3.5 |
| L-Aspartic acid | 0.22 |
| L-Glutamine | 6.0 |
| L-Glutamic acid | 6.0 |
| L-Leucine | 0.76 |
| L-Lysine | 6.24 |
| L-Methionine | 0.5 |
| L-Proline | 3.5 |
| DL-Serine | 11.0 |
| L-Threonine | 1.75 |
| L-Tyrosine | 0.5 |
| L-Valine | 1.0 |
| Sucrose | 381.8 |
| Glucose | 7.0 |
| MES | 19.5 |
| with the pH being adjusted to | 6.15. |

By yet another feature of the process of this invention the fermentation medium for the production of hyphal bodies, of *Entomophaga aulicae* which form conidia has the following composition:

| Compound | Concentration g/10 L |
|---|---|
| $NaH_2PO_4.H_2O$ | 10.13 |
| KCl | 41.0 |
| $CaCl_2$ | 7.5 |
| $MgCl_2.6H_2O$ | 22.8 |
| $MgSO_4$ | 13.5 |
| $NaHCO_3$ | 3.5 |
| L-Asparagine | 3.5 |
| L-Aspartic acid | 3.5 |
| L-Cystine | 0.22 |
| L-Glutamine | 6.0 |
| L-Glutamic acid | 6.0 |
| L-Leucine | 0.76 |
| L-Lysine | 6.24 |
| L-Methionine | 0.5 |
| L-Proline | 3.5 |
| DL-Serine | 11.0 |
| L-Threonine | 1.75 |
| L-Tyrosine | 0.5 |
| L-Valine | 1.0 |
| Sucrose | 100.0 |
| Glucose | 0.3 |
| MES | 19.5 |
| Tryptic soy broth | 80.0 |
| Calcium caseinate | 40.0 |
| with the pH being adjusted to | 6.15. |

By a further feature of this invention, the hyphal body yield is $3.5\pm1.5\times10^9$ for a 10 L fermentation run.

By another feature of the process of this invention, the process is accomplished as a batch fermentation process.

By other features of the process of this invention, the inoculum comprises a single protoplast type; or comprises a combination of protoplast types; or comprises a walled stage or a combination of walled stages; or comprises a combination of protoplast and walled stages.

By still other features of the process of this invention, the inoculum consists of walled stages which are later in the developmental sequence than spindle-shaped protoplasts, wherein the protoplasts will revert to spindle-shaped protoplasts; or the inoculum comprises a walled stage; or the inoculum comprises a combination of walled stages; or the inoculum comprises a combination of protoplast and walled stages.

By still other features of the process of this invention, the inoculum consists of walled stages, so that the walled stages will release spindle-shaped protoplasts; or the inoculum consists of walled stages, so that the walled stages will release catenulate spindle-shaped protoplasts.

By yet other features of the process of this invention, a function of the calcium caseinate, which is included in the medium, is that of a stabilizing agent against stress for protoplast stages and for walled stages during the initial period of wall deposition by means of physical adherence of the molecules by virtue of their size, conformation and charge distribution onto the outer surface of the protoplast stage or the walled stage.

By another feature of the process of this invention, initial conidia are formed while the mass fermentation is in progress, and the conidia are detected by light microscope examination of an aliquot of the medium.

By another feature of the process of this invention, the procedure includes the step of determining when to harvest hyphal body fermentation products by detecting initial conidia as this indicates that the necessary genetic and biochemical "triggers" have occurred to commit the hyphal bodies to conidium formation.

By another feature of the process of this invention, the initial sedimentation is at one G for 1 h, the further sedimentation is at one G for 1 h, the suitable vessel is a 1 L graduated cylinder, the final hyphal body volume is about 125 mL/10L fermentation, and the hyphal body yield is found to be $3.5\pm1.5\times10^9$ for a 10 L fermentation.

d) Generalized Description of the Invention

The tryptic soy broth, which contains both a pancreatic digest of casein and a papain digest of soybean meal, was chosen as a basal medium supplement because it was known to be a good, inexpensive source of amino acids and could also function as a source of trace elements and growth factors.

A serum albumin was chosen as the protoplast stabilizing agent to replace fetal calf serum not only because it is less costly but because serum albumins are well-characterized, single chain polypeptides which are negatively charged in the pH range utilized (see, Nolan et al., Condor 77:154–159, 1975; and Prager et al., J. Mol. Evol. 3:243–262, 1974).

Calcium caseinate was chosen as the stabilizing agent to replace albumin not only because it, in turn, was less costly but because of its known primary structure (see, Swaisgood, in "Developments In Dairy Chemistry-1. Proteins". 1982. pp.1–59; Ribadeau-Dumas, in "Milk Proteins. Nutritional, Clinical, Functional and Technological Aspects". 1989. pp.112–123) and the high negative charges of $\alpha S1$-, $\alpha S2$-, $\beta$- and $\kappa$-caseins in the pH range utilized (see Schmidt, in "Developments In Dairy Chemistry-1. Proteins. 1982. pp.61–86; and Swaisgood, in Milk Proteins. Nutritional, Clinical, Functional and Technological Aspects". 1989. pp.192–210) and its heat stability (Fox, in "Developments In Dairy Chemistry-1. Proteins". 1982. pp.189–228).

By broad features of the present invention, it has been found that the growth medium allows a mixed protoplast inoculum to develop through a series of protoplast stages to form walled spherical and rod-shaped hyphal bodies which then form conidia from the protoplast inoculum are formed in a single batch fermentation run. The hyphal bodies are the stages which are sprayed in the forest. The conidia, upon germination, infect the insect larvae.

BRIEF DESCRIPTION OF THE DRAWINGS

In the accompanying drawings,

FIGS. 3–6 are photomicrographs of *E. aulicae* (isolate FPMI 931) developmental stages produced in basal medium+0.8% tryptic soy broth+0.4% calcium caseinate under fermentation conditions and the bars=20 µm, in which FIG. 3 shows clumps of spherical hyphal bodies; FIG. 4 shows a rod-shaped hyphal body; FIG. 5 shows a rod-shaped hyphal body bearing conidium (arrowhead); and FIG. 6 shows two conidia after discharge into medium.

Figure 1:
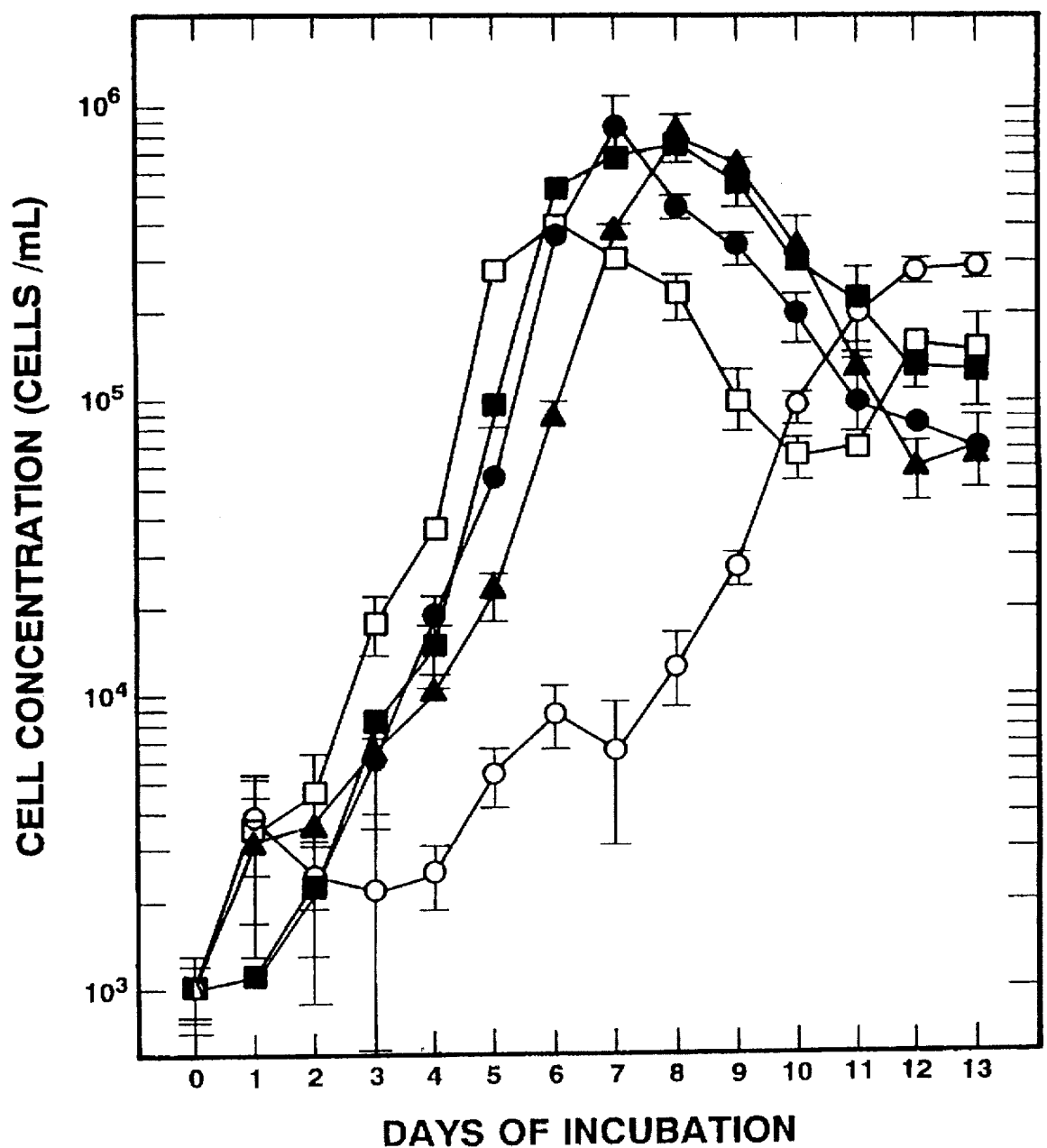
FIG. 1 is a graph showing the correlation between *E. aulicae* (isolate N100) cell concentration, the level of albumin added to the basal medium plus 0.8% TSB and the period of incubation under fermentation conditions. Albumin concentrations:0% (no growth, not shown), 0.1% (open circles), 0.2% (open squares), 0.4% (solid triangles), 0.8% (solid circles) and 1.0% (solid squares).

DESCRIPTION OF PREFERRED EMBODIMENTS (a) Description of Materials Used

Before describing the present invention in terms of examples, the following description of the materials used will be given.

MATERIALS

Protoplasts of the fungus *E. aulicae* (isolates N100 and FPMI 931) were maintained in Grace's insect tissue culture medium (described hereinabove) supplemented with hematin (0.5 µg/mL). These cultures were incubated at 20°±1° C. in 30 mL T flasks and transferred weekly.

Chemicals, unless otherwise indicated, were reagent grade (obtained from Sigma). Other chemicals and their sources were: bovine serum albumin (Cohn Fraction V, obtained from Sigma); heat-inactivated fetal calf serum (FCS) (obtained from GIBCO/BRL, Burlington, Ontario); TC YEASTOLATE™ and tryptic soy broth (TSB) (obtained from DIFCO™); Yeast Extract (BBL); spray-dried calcium caseinate (Lot # J1-319-2, obtained from Amcan Ingredients, Toronto, Ontario).

The procedure for preparing filter-sterilized TSB for use in the medium of the present invention is as follows: the TSB was filter-sterilized in order not to destroy heat-labile amino acids and growth factors. This process involves the filtering of the TSB at a concentration of 80 gm in one liter of distilled water through the following sequence: (a) gravity filtration through a 27 cm Whatman™ No. 1 filter circle in a glass funnel, (b) gravity filtration through a 24 cm Whatman™ No. 5 filter circle in a glass funnel, (d) vacuum filtration through sterile Nalgene™ 500 mL filter sterilization units with 0.45 µm filters, and (e) vacuum filtration through sterile Nalgene™ 500 mL filter sterilization units with 0.2 µm filters.

The control medium consisted of a highly modified Grace's medium containing 13 amino acids described above and designated basal medium (BM) and supplemented with 2.8% fetal calf serum (FCS). Sucrose was used as the osmotic stabilizer. The osmolality was maintained at an optimal level of 350±2 mosmol/kg.

b) General Example I

The general fermentation conditions were as follows:

Inocula for shaken flask and fermentation culture were produced as follows:

Protoplasts of the fungus *E. aulicae* (isolate N100) were maintained as described hereinabove and inocula were produced by transferring 0.1 mL of a protoplast suspension from a stock culture to 49.9 mL of either GM plus FCS or GM plus H in 125 mL BELLCO™ flasks. The inoculum cultures were incubated for 144 h as shaken cultures (50 rpm; PSYCROTHERM™ model G-27, New Brunswick Scientific Company, Edison, N.J.) in darkness at 20° C and 150 mL of the resulting growth (contents of three flasks) was used as the inoculum for a single fermentation run. The low inoculum volume and protoplast count minimized nutrient carry-over but allowed excellent growth. The inoculum level, in approximately 150 mL, was adjusted to give an initial concentration of $10^3$ protoplasts/mL in 10 L of medium in the 14 L capacity fermentation vessel.

Three growth conditions were used in the examples of this invention: (1) small scale shaken flasks (50 mL medium/125 mL flask); (2) large scale shaken flasks (200 mL medium/1 L flask); and (3) fermentation conditions (10 L of medium/ 14 L fermentation vessel). Flask cultures were incubated in darkness on a gyratory shaker (50 rpm, 20° C; PSYCROTHERM™ model G-27, New Brunswick Scientific, Edison, N.J.). During fermentation runs: (1) aeration was maintained at 1 L/min (0.1 v/v/m); (2) impeller blade speed was maintained at 100 rpm, and (3) the temperature was kept at 19±1° C. Sample removal and clarification was as in Nolan (Can. J. Microbiol. 32:855–860, 1986).

Two analyses of pH and dissolved oxygen concentration were conducted on each sample. Sucrose and protein levels were not analyzed. Dissolved oxygen levels were determined by using either the polarographic oxygen (Clark type) electrode technique using the protocol of Nolan (Can. J. Bot. 68:2708–2713, 1990) or the $_pO_2$ electrode of a Ciba Corning Model 238 pH/Blood Gas Analyzer (Ciba Corning Canada Inc., Richmond Hill, Ontario). Changes in the concentration of ninhydrin-positive compounds (NPC) were determined using a Beckman Spinco automatic analyzer (model 121 MB, coupled with a Beckman System AA Integrator, Spinco Division, Beckman Instruments, Inc., Palo Alto, Calif.) as described in Nolan (Mycologia, 68:523–540, 1976) with each value being the average of two separate determinations.

The cell counts were made with a hemacytometer, with four counts being made for each sample. Dry weights were not determined. The final hyphal body product was harvested by sedimentation (1 h, 1×g) in the vessel, decanting most of the supernatant, followed by further sedimentation (1 h, 1×g) in a 1 L graduated cylinder (final hyphal body volume approximately 125 mL/10 L run). All graph values represent the mean ± standard error of the mean. Statistical comparisons were made using ANOVA (MINITAB™).

c) EXPERIMENTS

EXPERIMENT A, EFFECTS OF HEMATIN

Because it is known that hematin enhances *E. aulicae* protoplast growth and hyphal body formation in stationary and small scale shaken cultures, isolate N100 was grown in BM+hematin (0.5 µg/mL) at the fermentation level. No growth occurred under these conditions. On the other hand, the control (BM+2.8% FCS) yielded $3.4 \times 10^4$ cells/mL on day 4 and $4.2 \times 10^8$ hyphal bodies on the bottom of the vessel on day 9.

EXPERIMENT B, USE OF INSECT CELL GROWTH MEDIUM

The protoplasts and hyphal bodies of *E. aulicae* are primarily produced in lepidopteran hosts. One medium, in particular, has been developed for the mass fermentation growth of lepidopteran (*Spodoptera frugiperda*) cells in the absence of sera (Inlow et al., J. Tissue Culture Methods 12:13–16, 1989). Its development was predicated upon the assumptions that (1) albumin is functionally the most important component of sera and that (2) the critical attribute of albumin is its binding of fatty acids (Goodman, J. Am. Chem. Soc. 80:3892–3898, 1958). The ability of isolate N100 to grow in small scale shaken cultures on this medium and its individual or variously combined components as supplements to BM:(1) BM+0.4% YEASTOLATE™+0.082 mg % cholesterol+0.036 mg % α-tocopherol+0.18 mg % cod liver oil fatty acid methyl esters+0.46 mg % TWEEN™ 80+0.1% PLURONIC™ polyol F68; (2) BM+0.082 mg % cholesterol+0.036 mg % α-tocopherol+0.18 mg % cod liver oil fatty acid methyl esters+0.46 mg % TWEEN™ 80; (3) BM+0.082 mg % cholesterol; (4) BM+0.036 mg % α-tocopherol; (5) BM+0.18 mg % cod liver oil fatty acid methyl esters; and (6) BM+0.46 mg % TWEEN™ 80 was determined. No growth occurred in any of the above during a 14 day incubation period.

EXPERIMENT C, GLUCOSE-YEAST EXTRACT MEDIA

The ability of isolate N100 protoplasts to produce hyphal bodies in both autoclaved and filter-sterilized glucose-yeast extract media (% glucose: % yeast extract of 6:2, 6:1, 4:2, 4:1, 3:2 and 3:1) was tested in large scale shaken cultures. The osmolalities for these filtered/autoclaved combinations were: 460/452, 402/394, 345/339, 287/282, 287/283 and 230/226 mosmol/kg, respectively. No growth or hyphal body production occurred under any of these conditions.

Experiments D–L

The following fermentations for *E. aulicae* (isolate N-100) were carried out under the above-described fermentation conditions:

D) Basal medium+2.8% FCS:day 4 yield=$3.4 \times 10^4$ protoplasts/mL;

E) Basal medium: no growth

F) Basal medium+hematin: no growth

G) Basal medium+0.8% TSB: no growth

H) Basal medium+0.8% albumin: grows for 2 days, then dies

I) Basal medium+0.8% dextran: no growth

J) Basal medium+0.8% dextran+0.8% albumin: grows for 2 days, dies

K) Basal medium+0.4% albumin+0.8% TSB: day 8 yield=$8.1 \times 10^5$ protoplasts/mL; day 13 hyphal body yield—$8.3 \times 10^8$ L) Basal medium+0.4% calcium caseinate+0.8% TSB: days 2–3 yield=$2.5 \times 10^5$ protoplasts/mL; day 9 hyphal body yield=$3.1 \times 10^9$ (using isolate FPMI 93I).

It will be seen from these results that the addition of TSB alone (prepared as described hereinabove) in the basal medium resulted in no growth. The addition of albumin+TSB (prepared as described hereinabove) resulted in a hyphal body yield, at the end of growth in 13 days, of $8.3 \times 10^8$. As seen in the results of Experiment L, fermentation in the medium of the present invention resulted in a hyphal body yield, at the end of growth in only 9 days, of $3.1 \times 10^9$. Thus, not only is there almost 4 times as much hyphal body growth using the growth medium of the present invention as compared to other media, but such growth takes place in only 9 days, i.e. in 49% less time.

In contrast to the above Example, the previously-described Doern et al paper, does not teach the use of a tryptic soy broth (formulated as described above for use in the fermentation medium of the present invention) as a medium useful for the growth fungi, particularly yeast. Doern et al prepares his TSB according to the recommendations of the manufacturers. TSB, as prepared by Doern et al, is by a procedure which includes the instructions: sterilize in the autoclave for 15 minutes at 15 pounds pressure (121° C). As shown by the following fermentation test results, this procedure brings about the loss of any heat-labile compounds.

d) Examples

EXAMPLE 1

Use of Albumin and Dextran as FCS Replacements

Dunphy and Nolan (Can. J. Microbiol. 28:815–821, 1982) had reported that 2.8% FCS could be replaced by 0.4% albumin in small scale shaken cultures of *E. aulicae* and that although the rate of protoplast growth was decreased—higher levels of hyphal body production resulted. Isolate N100 was incubated under fermentation conditions in BM+0.8% albumin (concentration doubled to counteract additional shear forces). The protoplasts grew slowly for the first two days of incubation (highest count=$1.9 \times 10^3$ protoplasts/mL) and then died.

Ketis et al. (Proc. Natl. Acad. Sci. USA 77:3788–3790, 1980) found that DEXTRAN T-500™ could be used as a model membrane stabilizer and substitute at an equal concentration for albumin. Isolate N100 was incubated under fermentation conditions in BM+0.8% dextran. No growth occurred.

The possibility of combining the albumin and dextran was tried at the fermentation level using BM+0.8% dextran+0.8% albumin. The results mirrored those using BM+0.8% albumin.

EXAMPLE 2

Use of Tryptic Soy Broth

Although the use of BM+0.8% TSB did not support growth of isolate N100, the use of BM+0.8% TSB+0.4% albumin under fermentation conditions produced a peak yield of $8.1\times10^5$ protoplasts on day 8 (FIG. 1, solid triangles) and the sediment contained $8.3\times10^8$ hyphal bodies after 13 days of incubation.

EXAMPLE 3

Optimum Concentration of Albumin

The optimum concentration of albumin was determined using isolate N100 in separate fermentation runs containing 0, 0.1, 0.2, 0.4, 0.8 and 1.0% albumin added to BM+0.8% TSB during a 13 day incubation period (FIG. 1). No growth occurred when the albumin was omitted. The 0.1% albumin gave the slowest rate of growth with the highest yield ($2.8\times10^5$ protoplasts/mL) being achieved on day 13 (FIG. 1, open circles). The 0.2% albumin (FIG. 1, open squares) gave a better rate of growth; however, the maximum yield (day 6, $4.0\times10^5$ protoplasts/mL) was only slightly higher than for 0.1% albumin. Growth with 0.4, 0.8 and 1.0% albumin (FIG. 1, solid triangles, solid circles, and solid squares, respectively) gave roughly equivalent yields (8.1, 8.8 and $7.8\times10^5$ protoplasts/mL) with growth in the 0.8% albumin peaking one day earlier (day 7). Growth with 0.1, 0.2, 0.8 and 1.0% albumin did not produce hyphal bodies. Thus, the 0.4% albumin concentration was selected for future use.

EXAMPLE 4

Isolate FPMI 931 Growth and Hyphal Body Production

Figure 2:
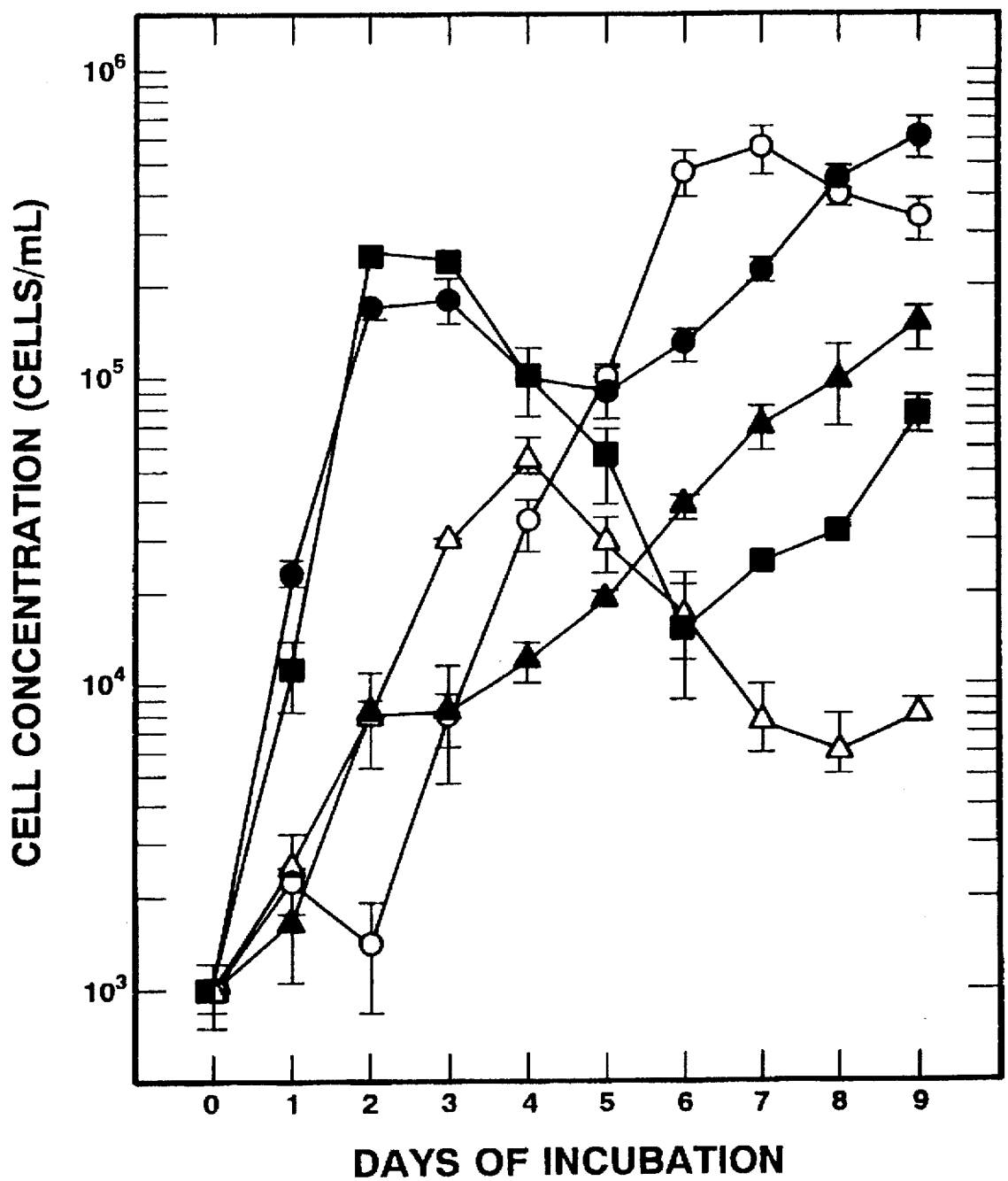
FIG. 2 is a graph showing the correlation between *E. aulicae* isolate N100 (open symbols) and isolate FPMI 931 (solid symbols) cell concentration, the growth medium and the period of incubation under fermentation conditions. Media used: basal medium (BM)+2.8% fetal calf serum (triangles), BM+0.8% TSB+0.4% albumin (circles), and BM+0.8% TSB+0.4% calcium caseinate (squares).

In order to determine the applicability of the results to other isolates, isolate FPMI 931 was selected. Isolate FPMI 931 grew more slowly in BM+FCS (FIG. 2, solid triangles) than did isolate N100 (FIG. 2, open triangles) and reached its highest yield ($1.5\times10^5$ protoplasts/mL) on the last day of incubation (day 9), whereas isolate N100 peaked on day 4 ($5.5\times10^4$ protoplasts/mL). Under these conditions, isolate FPMI 931 and isolate N100 produced $3.1\times10^7$ and $5.0\times10^8$ hyphal bodies, respectively, in the day 9 sediment. Isolate FPMI 931 grew more rapidly and reached two peaks [days 2–3 (1.7 and $1.8\times10^5$ protoplasts/mL) and day 9 ($6.1\times10^5$ protoplasts/mL)] in BM+TSB+albumin (FIG. 2, solid circle) as compared to isolate N100 which reached its peak yield ($5.6\times10^5$ protoplasts/mL) on day 7 (FIG. 2, open circles). Under these conditions, isolates FPMI 931 and N100 produced $7.5\times10^8$ and $8.3\times10^8$ hyphal bodies, respectively, in the day 9 sediment.

EXAMPLE 5

Use of Calcium Caseinate

Figure 3:
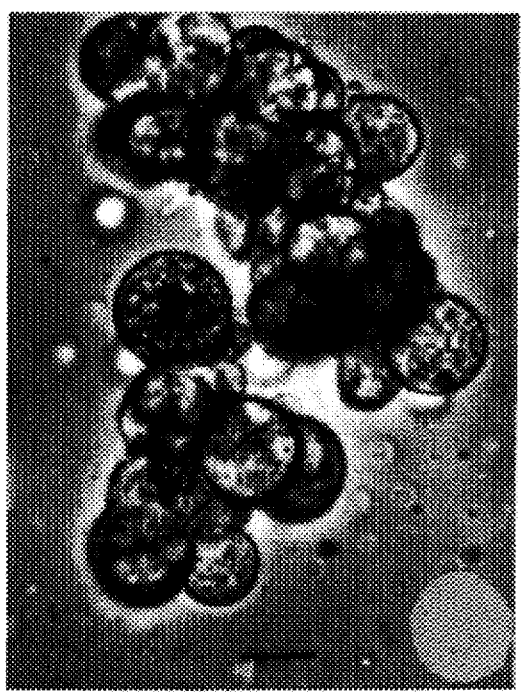
Figure 4:
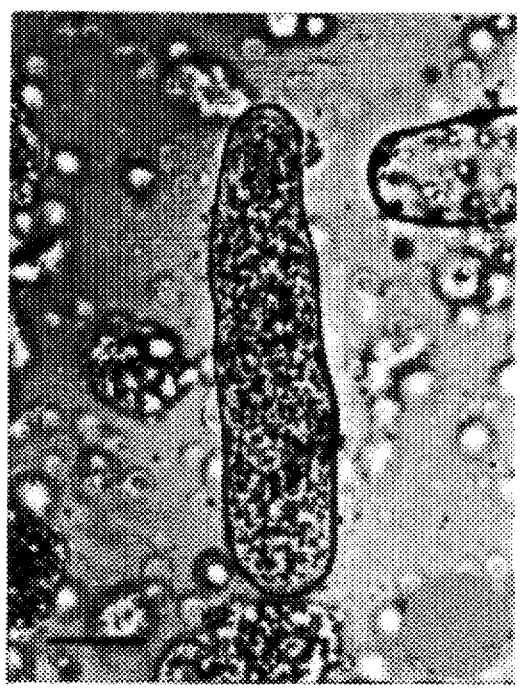
Figure 5:
Figure 6:
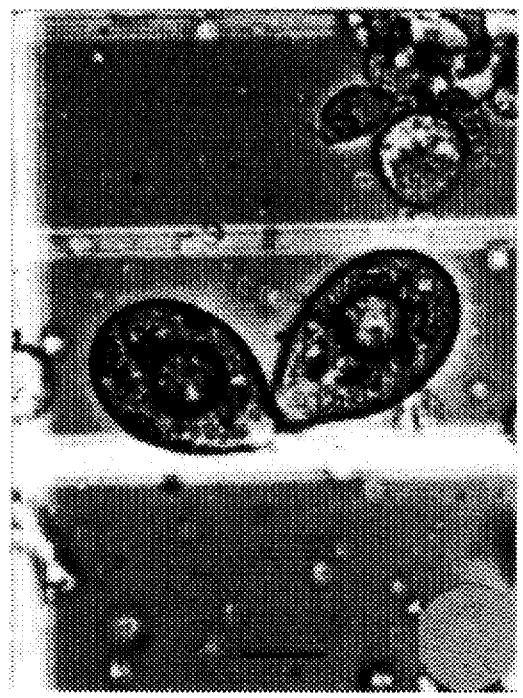

The use of calcium caseinate as a substitute for albumin at the fermentation level was tested using isolate FPMI 931. The growth in BM+0.8% TSB+0.4% calcium caseinate (FIG. 2, solid squares) reached two peaks [days 2–3 (2.5 and $2.4\times10^5$ protoplasts/mL) and day 9 ($7.6\times10^4$ protoplasts/mL)] and the hyphal body yield (day 9) was $3.1\times10^9$. Thus, growth in BM+TSB+calcium caseinate produced a high yield of spherical (17.5–42.5 μm diam., x=27±8.9 μm, n=18) and rod-shaped [25–102.5 μm long (x=53±19.9 μm)× 7.5–37.5 μm wide (x=16.8±6.8 μm), n=27] hyphal bodies (FIG. 3, 4, respectively). In addition, conidia [42.5–67.5 μm long (x=49.7±4.5 μm)×28.8–43.8 μm wide (x=36.6±3.5 μm), n=29] were produced by spherical (not shown) and rod-shaped hyphal bodies (FIG. 5, arrowhead) and could be found in the medium beginning on day 6 (FIG. 6). These conidia were produced by hyphal bodies both in the medium and in a ring-like area above the air/medium interface. Therefore, this medium produced hyphal bodies which were capable of producing conidia during fermentation growth and prior to greenhouse and field spraying.

Fermentation Run—HARVEST

After removal of the fermentation vessel, the contents were allowed to settle for 1 h after which the supernatant was removed until 900 mL remained. The sediment was then resuspended in this volume and a count was done. It was determined that the sediment contained $3.4\pm0.25\times10^6$ hyphal bodies/mL which, when multiplied by 900 mL gives a total count of $3.1\pm0.22\times10^9$ hyphal bodies. The sediment also contained $1.0\pm0.42\times10^4$ conidia/mL. The wet weight of the sediment was 59.41 gm. The material from the sides of the vessel (above the liquid level) was removed, resuspended in 50 mL of medium, and a count done. It was determined to contain $1.7\pm0.24\times10^5$ hyphal bodies/mL and $8.3\pm2.6\times10^3$ conidia/mL. The material was quite difficult to break apart and many large clumps remained intact, therefore the count was probably falsely low.

It is important that harvesting and subsequent dehydration of the hyphal bodies for storage be done in a manner that preserves them in a state from which, upon rehydration, mature conidia are formed and are discharged. In preliminary studies, the protocol of McCabe et al (see U.S. Pat. No. 4,530,834) has been used to advantage; however, more work with *Entomophaga aulicae* is required.

Generalized Synopsis of the Invention

In many representatives of the Entomophthorales, hyphal bodies are initially produced both in vivo and in vitro by hyphal fragmentation but may subsequently undergo fission or budding. In *E. aulicae*, hyphal bodies can be formed either as a consequence of protoplast morphogenesis in vitro or in vivo or by the fragmentation of hyphae formed during resting spore germination under special conditions in vitro. A general description of some of the early entomophthoralean studies can be found in Nolan, Fungal Protoplasts. Applications in biochemistry and genetics. pp.87–112, 1985.

The *E. aulicae* hyphal body wall consists of a single layer with a fibrillar structure (Beauvais et al., J. Gen. Microbiol. 135:489–498, 1989). For all representatives of the Entomophthorales examined, the walls were composed primarily of β(1-3) glucan and chitin (Latge and Beauvais, J. Invertebr. Pathol. 50:53–57, 1987). Studies concerning the distribution of chitin and β(1-3) glucan synthases in the protoplasts and hyphal bodies of *E. aulicae* show that both enzymes were active in the hyphal bodies; whereas, chitin synthase activity was absent and only a very low level of β(1-3) glucan synthase activity was detected in the protoplasts. The absence of wall synthesis in protoplast cultures was postulated to be the result of a continuous inhibition of the two enzyme systems by intracellular compounds and that glucan synthase, in particular, is inhibited by such medium components as NaCl and FCS (Beauvais and Latge, Arch. Microbiol. 152:229–236, 1989). This hypothesis does not explain the ability of all non-senescent *E. aulicae* isolates, with the exception of developmental mutants (Nolan, Can. J. Microbiol. 32:855–860, 1986) and those exposed to development altering growth conditions (Nolan, Can. J. Bot. 69:2578–2581, 1991) to proceed through the spindle-shaped protoplast to hyphal body morphogenetic sequence in the presence of FCS. In addition, the protoplast developmental sequence as given in Beauvais et al. (1989 reference hereinabove) is incomplete with the late fusion sphere stage totally absent and with the early fusion sphere stage unwinding to once more give rise to a chain of spindle-shaped protoplasts. The chain of spindle-shaped protoplasts gives rise to the early fusion sphere and, thus, what is apparently happening is the creation of a developmental loop with an alternation between spindle-shaped protoplasts and early fusion spheres. The reversion of early fusion spheres to spindle-shaped protoplasts, in this case, indicates unfavourable growth conditions.

As noted hereinabove there have been disclosures of a variety of media to produce entomophthoralean resting spores. *Entomophthora planchoniana*, which also produces resting spores, has been shown to produce overwintering hyphal bodies which subsequently produce conidia (Keller, J. Invertebr. Pathol. 50:333–335, 1987) and this may help to explain the ability of several entomophthoralean fungi, including *E. aulicae*, to survive in desiccated larval cadavers. It has been found that the survival of *E. aulicae* hyphal bodies occurred in desiccated larval cadavers of the spruce budworm at 4° C. after 84 days (longest period tested) and in the cabbage looper at 4° C. and −20° C after 13 months (Tyrrell, J. Invertebr. Pathol. 52:187–188, 1988). Entomophthoralean hyphal bodies produced in vitro can be stored, at present, for only short periods. It has been found that *Erynia neoaphidis* hyphal bodies remained viable for 2 months at 4° C when mixed with some moistened clays or when left attached to certain nutrient supports (e.g. rice) (Latge et al., In Aphid antagonists. 1983. pp.20–32). A protocol which has been developed for storing mass-produced mycelia of *Erynia radicans* (McCabe and Soper, U.S. Pat. No. 4,530, 834).

Some problems encountered in the use of hyphal bodies in biocontrol programs have also been examined. Hyphal bodies of *Erynia neoaphidis* (isolate 64) which had been produced on a 6% glucose-2% yeast extract medium in a 16 L fermenter have been utilized. In field studies with aphids (esp. *Metopolophium dirhodum*) on wheat, 6 g of dry mycelium in 40 L of water was applied to 100 $m^2$ plots. This inoculum produced in excess of 450 primary and secondary conidia per $mm^2$. In spite of favorable weather and high levels of conidia ($LC_{50}$=15 conidia/$mm^2$), it has been found that the levels of infection were not significantly higher in treated plots as compared to untreated plots. Aphid infection by treatment did occur, however, because of six cultures of *E. neoaphidis* obtained from infected aphids three were of isolate 64 (Latteur and Godefroid, In Aphid antagonists. 1983. pp.2–10). In greenhouse trials against aphids on lettuce and eggplant, inoculum levels of 10, 20, 40 and 300 g mycelium (wet weight)/$m^2$, were used and these dosages resulted in final aphid mortality levels of 66% (45 days), 1% (30 days), 4% (20 days) and 20 to 38% (18 days), respectively. Even infection levels of 20% were not sufficient to stop the development of aphid populations, particularly *Aphis solani* on lettuce. These results suggested that if dramatic results were to be expected shortly after application then the level of the target aphids would have to be higher (Latge et al., In Aphid antagonists. 1983. pp.20–32). Latteur and Godefroid (reference hereinafter) found that the population density for the two species present (*M. dirhodum* and *Sitobion avenae*) did not exceed an average value of 5 insects per species per wheat stalk. Isolate 64 was initially chosen for its ability to grow rapidly in a liquid medium and for its high infectivity for aphids. However, this isolate produces little growth in infected hosts and, thus, subsequently forms few conidia which gives it a limited capacity to spread within the aphid population (Wilding et al., In Fundamental and applied aspects of invertebrate pathology. 1986. pp.159–162). It has been found that abundant conidia have been formed on infected hosts by *E. aulicae* isolates. An *E. aulicae* infected spruce budworm larva produced $10^6$ conidia within 3 to 4 days of infection (Perry and Regniere, In Fundamental and applied aspects of invertebrate pathology. 1986. pp.167–170).

In fermentation runs using BM+FCS, the hyphal body yields for isolates N100 and FPMI 931 were 3.5±1.9×$10^8$ and 31±0.0×$10^7$ respectively, with the medium costing $CAN149.86. In fermentation runs using BM+TSB+albumin, the hyphal body yields for isolates N100 and FPMI 931 were 5.35±2.95×$10^8$ and 7.5±0.0×$10^8$, respectively, with the medium costing $CAN61.73. In fermentation runs using BM+TSB+calcium caseinate, the hyphal body yield for isolate FPMI 931 was 3.5±1.5×$10^9$ with the medium costing $CAN35.13.

The BM+0.8% TSB+0.4% calcium caseinate growth medium of an aspect of this invention is a major breakthrough in that: (1) the *E. aulicae* developmental sequence from protoplast inoculum to hyphal bodies competent to form conidia can be carried out in a batch fermentation process, (2) by examining the fermentation product it can be determined if conidia can be produced prior to engaging in expensive field spraying, (3) this medium supports the growth of *E. aulicae* isolates from widely separated geographical areas, (4) the medium is relatively inexpensive, (5) the hyphal bodies are easily separated from the spent medium, (6) the hyphal body yield is high, and (7) the hyphal bodies can withstand a variety of spray techniques.

The basis of the present invention is the discovery that added protein [fetal calf serum, (FCS)] was not required in media for *Entomophaga aulicae* protoplast growth in small-scale shaken cultures and that protein (FCS) was required for protoplast.

The inventor discovered that, at the small-scale shaken flask level and at the fermentation level, the protein components of FCS were not utilized. Thus, the added non-denatured proteins were not being utilized as nutrients. With the non-requirement for added protein at the small-scale level and with its requirement under fermentation conditions and given its lack of a role as a nutrient, the role of the FCS proteins is believe to be that of protoplast membrane stabilizers.

It has heretofore been felt that albumin is the most important protein in FCS and that this importance derives from its role in binding fatty acids. Thus, albumin would be chosen as a replacement for FCS for its ability to supply fatty acids. However, in the case of *Entomophaga aulicae*, added fatty acids are not required for growth and their addition will not replace the need for the protein(s). Dextran T-500™ would substitute for albumin stabilizing model membranes; however, dextran will not work as an albumin substitute for *E. aulicae*. Thus, the protein used in the stabilization process must possess some very specific attributes.

The realization of the role of non-denatured protein(s) with specific charges was discovered by the inventor as a result of studies involving the use of charged surfaces within the fermentation vessel, and the use of calcium caseinate was discovered by the inventor as a result of the comparison of its charge characteristics with albumin and the ability to autoclave sterilize calcium caseinate (40 gm in 2 L of distilled water in a 4 L flask, 121° C., 20 min) as a result of its heat stability. Calcium caseinate, like FCS proteins and albumin, is not utilized as a nutrient.

The filter-sterilized TSB used herein was based on the discovery, by the present inventor, that the role of the tryptic soy broth was that of an inexpensive source of amino acids, trace elements, and growth factors.

Thus, in summary, the non-denatured, non-nutrient protein component functions as a very specific type of protoplast stabilizer under fermentation shear conditions and the TSB provides the additional amino acids, growth factors, and trace elements required under high-stress fermentation conditions.

Glossary

GLOSSARY

BM: basal medium

FCS: fetal calf serum

FPMI 931: an isolate of *Entomophaga aulicae* from larval spruce budworm from Black Sturgeon, Ontario, Canada GM: Grace's medium H: hematin MES: a buffer, (2-[N-Morpholino]ethanesulfonic acid)

N100: an isolate of *Entomophaga aulicae* from larval eastern hemlock looper from Bauline Line, Avalon Peninsula, Island of Newfoundland, Canada SMA: Sabouraud maltose agar TSB: tryptic soy broth Conclusion Although the present invention has been described in terms of the presently preferred embodiments, it is to be understood that such disclosure is not to be interpreted as limiting. The specific medium ingredients and their concentrations may be altered to accomplish specific desired purposes. Various alterations and modifications will no doubt become apparent to those skilled in the art after having read the above disclosure. Accordingly, it is intended that the claims be interpreted as covering all alterations and modifications that fall within the spirit and scope of the invention.

Publications

The following are publications which relate to general aspects of the present invention.

1) Beauvais, A., and Latge, J.-P. 1988. "A Simple Medium for Growing Entomophthoralean Protoplasts." J. Invertebr. Pathol. 51:175–178.

2) Beauvais, A., and Latge, J.-P. 1989. "Chitin and B(1-3)-Glucan Synthases in the Protoplastic Entomophthorales." Arch. Microbiol. 152:229–236.

3) Beauvais, A., Latge, J.-P., Vey, A., and Prevost, M.-C. 1989. "The Role of Surface Components of the Entomopathogenic Fungus *Entomophaga aulicae* in the Cellular Immune Response of *Galleria mellonella* (Lepidoptera)." J. gen. Microbiol. 135:489–498.

4) Dunphy, G. B., and Nolan, R. A. 1982. "Simplified Growth Media for *Entomophthora egressa* Protoplasts." Can. J. Microbiol. 28:815–821.

5) Fox, P. F. 1982. "Heat-Induced Coagulation of Milk." in "Developments in Dairy Chemistry-1. Proteins." Edited by P. F. Fox. Applied Science, London. pp. 189–228.

6) Goodman, D. S. 1958. "The Interaction of Human Serum Albumin With Long-Chain Fatty Acid Anions." J. Am. Chem. Soc. 80:3892–3898.

7) Grace, T. D. C. 1962. Establishment of "Four Strains of Cells From Insect Tissue Grown In Vitro." Nature (London), 195:788–789.

8) Groner, A. 1975. "Production of Resting Spores of *Entomophthora thaxteriana*." J. Invertebr. Pathol. 26:393–394.

9) Inlow, D., Shauger, A., and Maiorella, B. 1989. "Insect Cell Culture and Baculovirus Propagation in Protein-Free Medium." J. Tissue Culture Methods 12:13–16.

10) Keller, S. 1987. "Observations on the Overwintering of *Entomophthora planchoniana*." J. Invertebr. Pathol. 50:333–335.

11) Ketis, N. V., Girdlestone, J., and Grant, C. W. M. 1980. "Positive Cooperativity in a (Dissected) Lectin-Membrane Glycoprotein Binding Event." Proc. Natl. Acad. Sci. USA 77:3788–3790.

12) Latge, J.-P., and Beauvais, A. 1987. "Wall Composition of the Protoplastic Entomophthorales." J. Invertebr. Pathol. 50:53–57.

13) Latge, J.-P., Silvie, P., Papierok, B., Remaudiere, G., Dedryver, C. A., and Rabasse, J. M. 1983. "Advantages and Disadvantages of *Conidiobolus obscurus* and of *Erynia neoaphidis* in The Biological Control of Aphids." in "Aphid Antagonists." Edited by R. Cavalloro. Balkema, Rotterdam. pp. 20–32.

14) Latteur, G., and Godefroid, J. 1983. "Trial of Field Treatments Against Cereal Aphids With Mycelium of *Erynia neoaphidis* (Entomophthorale) Produced In Vitro. in "Aphid Antagonists." Edited by R. Cavalloro. Balkema, Rotterdam. pp. 2–10.

15) Murrin, F., and Nolan, R. A. 1987. "Ultrastructure of the Infection of Spruce Budworm Larvae by the Fungus *Entomophaga aulicae*." Can. J. Bot. 65:1694–1706.

16) Nolan, R. A. 1976. "Physiological Studies on an Isolate of *Saprolegnia ferax* From the Larval Gut of the Blackfly *Simulium vittatum*." Mycologia, 68:523–540.

17) Nolan, R. A. 1985. "Protoplasts From Entomophthorales." in Fungal Protoplasts. Applications in Biochemistry and Genetics." Edited by J. F. Peberdy and L. Ferenczy. Marcel Dekker, New York. pp.87–112.

18) Nolan, R. A. 1986. "Effects of an Altered Developmental Pattern on Amino Acid Uptake For a Protoplast Isolate of the Fungus *Entomophaga aulicae* Under Mass-Fermentation Conditions." Can. J. Microbiol. 32:855–860.

19) Nolan, R. A. 1988. "A Simplified, Defined Medium For Growth of *Entomophaga aulicae* Protoplasts." Can. J. Microbiol. 34:45–51.

20) Nolan, R. A. 1990. "Enhanced Hyphal Body Production by *Entomophaga aulicae* Protoplasts in the Presence of a Neutral and a Positively Charged Surface Under Mass Fermentation Conditions." Can. J. Bot. 68:2708–2713.

21) Nolan, R. A. 1991. "Influence of a Negatively Charged Surface (TEFLON™ Disk) on *Entomophaga aulicae* Protoplast Morphogenesis Under Mass Fermentation Conditions. Can. J. Bot. 69:2578–2581.

22) Nolan, R. A., and Dunphy, G. B. 1979. "Effects of Hormones on *Entomophthora egressa* Morphogenesis." J. Invertebr. Pathol. 33:242–248.

23) Nolan, R. A., Dunphy, G. B., and MacLeod, D. M. 1976. "In vitro Germination of *Entomophthora egressa* Resting Spores." Can. J. Bot. 54:1131–1134.

24) Nolan, R. A., Brush, A. H., Arnheim, N., and Wilson, A. C. 1975. "An Inconsistency Between Protein Resemblance and Taxonomic Resemblance: Immunological Comparison of Diverse Proteins From Gallinaceous Birds." Condor 77:154–159.

25) Perry, D. F., and Regniere, J. 1986. "The Role of Fungal Pathogens in Spruce Budworm Population Dynamics: Frequency and Temporal Relationships. in "Fundamental and Applied Aspects of Invertebrate Pathology." Edited by R. A. Samson, J. M. Vlak and D. Peters. Foundation of the Fourth International Colloquium of Invertebrate Pathology, Wageningen. pp.167–170.

26) Prager, E. M., Brush, A. H., Nolan, R. A., Nakanishi, M. and Wilson, A. C. 1974. "Slow Evolution of Transferrin and Albumin in Birds According to Microcomplement Fixation Analysis." J. Mol. Evol. 3:243–262.

27) Ribadeau-Dumas, B. 1989. "Structure and Variability of Milk Proteins." in "Milk Proteins. Nutritional, Clinical, Functional and Technological Aspects." Edited by C. A. Barth and E. Schlimme. Springer, New York. pp.112–123.

28) Schmidt, D. G. 1982. "Association of Caseins and Casein Micelle Structure." in "Developments in Dairy Chemistry-1. Proteins." Edited by P. F. Fox. Applied Science, London. pp.61–86.

29) Swaisgood, H. E. 1982. "Chemistry of Milk Protein." in "Developments in Dairy Chemistry-1. Proteins." Edited by P. F. Fox. Applied Science, London. pp.1–59.

30) Swaisgood, H. E. 1989. "Structural Changes in Milk Proteins." in "Milk Proteins. Nutritional, Clinical, Functional and Technological Aspects." Edited by C. A. Barth and E. Schlimme. Springer, New York. pp.192–210.

31) Tyrrell, D. 1988. "Survival of *Entomophaga aulicae* in Dried Insect Larvae." J. Invertebr. Pathol. 52:187–188.

32) Wilding, N., Latteur, G., and Dedryver, C. A. 1986. "Evaluation of Entomophthorales For Aphid Control: Laboratory and Field Data." in "Fundamental and Applied Aspects of Invertebrate Pathology." Edited by R. A. Samson, J. M. Vlak and D. Peters. Foundation of the Fourth International Colloquium of Invertebrate Pathology, Wageningen. pp.159–162.

I claim:

1. In a process for the mass fermentation production of hyphal bodies which form conidia of the species *Entomophaga aulicae* the improvement comprising fermenting the fungus in a medium including, in addition to a basal medium, an additive consisting essentially of both 0.8% by weight filter sterilized tryptic soy broth prepared by dissolving tryptic soy broth in distilled water, gravity filtering the solution through a paper filter and then vacuum filtering the produced filtrate through a sterile membrane filtration unit and 0.4 by weight calcium caseinate.

2. The process of claim 1, wherein the composition of the basal medium is as follows:

| Compound | Concentration g/10 L |
|---|---|
| $NaH_2PO_4.H_2O$ | 10.13 |
| KCl | 41.0 |
| $CaCl_2$ | 7.5 |
| $MgCl_2.6H_2O$ | 22.8 |
| $MgSO_4$ | 13.5 |
| $NaHCO_3$ | 3.5 |
| L-Asparagine | 3.5 |
| L-Aspartic acid | 3.5 |
| L-Cystine | 0.22 |
| L-Glutamine | 6.0 |
| L-Glutamic acid | 6.0 |
| L-Leucine | 0.76 |
| L-Lysine | 6.24 |
| L-Methionine | 0.5 |
| L-Proline | 3.5 |
| DL-Serine | 11.0 |
| L-Threonine | 1.75 |
| L-Tyrosine | 0.5 |
| L-Valine | 1.0 |
| Sucrose | 381.8 |
| Glucose | 7.0 |
| MES | 19.5 |
| pH adjusted to | 6.15. |

3. The process of claim 1, wherein the composition of the fermentation medium is as follows:

| Compound | Concentration g/10 L |
|---|---|
| $NaH_2PO_4.H_2O$ | 10.13 |
| KCl | 41.0 |
| $CaCl_2$ | 7.5 |
| $MgCl_2.6H_2O$ | 22.8 |
| $MgSO_4$ | 13.5 |
| $NaHCO_3$ | 3.5 |
| L-Asparagine | 3.5 |
| L-Aspartic acid | 3.5 |
| L-Cystine | 0.22 |
| L-Glutamine | 6.0 |
| L-Glutamic acid | 6.0 |
| L-Leucine | 0.76 |
| L-Lysine | 6.24 |
| L-Methionine | 0.5 |
| L-Proline | 3.5 |
| DL-Serine | 11.0 |
| L-Threonine | 1.75 |
| L-Tyrosine | 0.5 |
| L-Valine | 1.0 |
| Sucrose | 100.0 |
| Glucose | 0.3 |
| MES | 19.5 |
| Tryptic soy broth | 80.0 |
| Calcium caseinate | 40.0 |
| pH adjusted to | 6.15. |

4. The process of claim 1 which is accomplished as a batch, uninterrupted, fermentation process.

* * * * *